United States Patent [19]

Dautzenberg et al.

[11] Patent Number: 4,664,105

[45] Date of Patent: May 12, 1987

[54] ABSORBING WOUND DRESSING AND METHOD FOR MAKING THE SAME

[75] Inventors: Horst Dautzenberg; Fritz Loth, both of Teltow; Bodo Borrmeister, Potsdam-Babelsberg; Dieter Bertram, Leipzig; Herbert Lettau, Halle-Neustadt, all of German Democratic Rep.; Jiri Stamberg; Jan Peka, both of Prague, Czechoslovakia

[73] Assignee: Veb Leipziger Arzneimittelwerk, Leipzig, German Democratic Rep.

[21] Appl. No.: 731,480

[22] Filed: May 7, 1985

Related U.S. Application Data

[63] Continuation of Ser. No. 412,858, Aug. 30, 1982, abandoned.

[30] Foreign Application Priority Data

Sep. 30, 1981 [DD] German Democratic Rep. ................................ 2336844

Nov. 11, 1981 [DD] German Democratic Rep. ................................ 2347334

[51] Int. Cl.$^4$ ............................................ A61K 31/74
[52] U.S. Cl. .................................. 128/156; 604/367; 604/375
[58] Field of Search .................. 604/376, 375, 368; 128/156, 155

[56] References Cited

U.S. PATENT DOCUMENTS

| | | | |
|---|---|---|---|
| 3,671,184 | 6/1972 | Cuculo | 604/364 |
| 4,136,697 | 1/1979 | Smith | 604/368 |
| 4,169,121 | 9/1979 | Pietsch et al. | 604/376 |
| 4,198,968 | 4/1980 | Kalberer et al. | 128/156 |
| 4,225,580 | 9/1980 | Rothman et al. | 424/78 |

Primary Examiner—C. Fred Rosenbaum
Assistant Examiner—Sherri E. Vinyard
Attorney, Agent, or Firm—Michael J. Striker

[57] ABSTRACT

The absorbing wound dressing which is atoxic, tissue compatible and very well adjusted to the shape of the wound, it is easily removable, protecting from infections or reduces infections in that it absorbs, in addition to the wound excudate, bacteria, fungi, toxins, proteins and inflammation mediators and which is therefore suitable for covering and cleaning of strongly wetting, infected wounds, as well as effected areas in skin and tissue diseases, consists of potentially macroporous particulate mixtures of regenerated cellulose and a carboxylate groups containing polysaccharide derivative. For making it, viscose solutions, which contain the polysaccharide derivative are thermically coagulated, purified and dried, after the deformation.

5 Claims, No Drawings

ABSORBING WOUND DRESSING AND METHOD FOR MAKING THE SAME

This is a continuation of application Ser. No. 412,858, filed Aug. 30, 1982 now abandoned.

BACKGROUND OF THE INVENTION

The invention relates to an absorbing wound dressing for covering and cleaning a strongly wetting, infected wound, as well as effected areas in skin and tissue diseases, as well as a method for making that dressing.

It is known that a modern wound dressing can be used in defective wounds of different genesis, particularly in problem indications, like Ulcus cruris, dekubitalulzera, diabetic gangrene, chronically infected wounds and burn wounds of 2nd and 3rd degree, whereby the wound dressing can be made toxically unobjectionable, without problems, able to be stored and it must be sterilizeable; furthermore, it must have a sufficient gas permeability for ventilation of the wound, it must adhere very well to the wound area without bonding itself to the scab of the wound, it must be characterized by a high degree of absorbability for wound healing features (wound exsudate, bacteria, necrotic cell material) and must be intensively wound cleaning and thereby infection reducing, and in addition it must be granulation and/or epithelisation effective.

It is also known that the conventional wound dressings which mainly consist of fabric or a texture made of natural or synthetic fibers, but above all, from regenerated cellulose in form of short or long fibers, do not meet completely the aforementioned criteria; in particular, they bond themselves to the wound or the scab of the wound, so that during the changing of the wound dressing the protective wound scab is torn open, the wound becomes irritated and the healing process is interrupted and naturally prolonged; furthermore its absorbability is limited, whereby in particular bacteria is not absorbed, so that consequently a reduction of the infection is very often only possible with added antibacterial substances, like antibiotics or sulfonamide.

To overcome these disadvantages, would dressings were developed (for example DD-PS 97547, DE-OS 1209702, DE-OS 1,254,295, DE-OS 1492409, DE-OS 1629425, U.S. Pat. No. 2,923,298, U.S. Pat. No. 3,012,918, U.S. Pat. No. 3,043,301, U.S. Pat. No. 3,285,245, U.S. Pat. No. 3,434,472, U.S. Pat. No. 3,438,371. U.S. Pat. No. 3,441,021, U.S. Pat. No. 3,446,208, U.S. Pat. No. 3,457,919, U.S. Pat. No. 3,579,628, U.S. Pat. No. 3,750,666) which on the wound side are provided with a non-adhering, flexible perforated plastic foil made of polyethylene, polypropylene, polyvinylchloride, polyvinylacetate, polyethylene terephthalate, ethylene/vinylacetate-copolymers, polyacrylates or polyvinylpyrrolidon; wound dressings are also known which are provided on the wound side, instead of the perforated plastic foil, equally effective thin perforated metal foils made from silver, aluminum or zinc (for example, DE-OS 1161384, DE-OS 1417379, U.S. Pat. No. 3,934,066). Such wound dressings do not bond themselves to the wound, they also permit the wound exsudate to permeate through the perforations so that it can be absorbed by the provided absorbing layers (cellulose, molded cotton, cotton felt). Apart from this fact that the absorbability of such wound dressings is not basically increased, the smearing-purulent exsudatees of strongly infected wounds can also block the openings, thus creating exsudate products which offer excellent growth capabilities for bacteria; one additional disadvantage, which cannot be completely excluded, is the friction effect of such wound dressings which are provided with metal layers.

An increased absorbability of the wound dressings is obtained by using such natural or synthetic materials which are water insoluble, on the one hand, but swell with water. Such materials are, for example, Chitin and Chitosan (MIT Sea Grant Rep. MIT SG 1978, Proc. Int. Conf. Chitin/Chitosan 1977, pages 296–305), collagen (DD-PS 56587, GB-PS 1195062, U.S. Pat. No. 3471598, U.S. Pat. No. 3,491,760, U.S. Pat. No. 3,800,792, U.S. Pat. No. 4,089,333), wet cross linked cellulose fibers, particularly formalized cotton and synthetic silk fibers (DE-OS 1492365), which advantageously contain 5–20 mass-% of the Na-salt of the carboxymethyl cellulose (CMC) (DE-OS 2638654), mixed fibers from regenerated cellulose and Na-CMC (U.S. Pat. No. 3,858,585) or cross linked CMC-products (DE-OS 2357079), hydrolyse products of cross linked copolymer from vinyl ester and unsaturated carbonic acids (DE-OS 2653135), cross-linked polyacrylamide and sulfonized polystyrole (DE-OS 1617998, DE-OS 1642072, U.S. Pat. No. 3,669,193), cross linked poly-N-vinylpyrrolidone and morpholinone (U.S. Pat. No. 3,810,468), cross linked dextrane, starches and starch derivatives (DD-PS 109513, DE-OS 2403269), as well as foam materials made from urea/formaldehyde or melamin/formaldehyde resins (DE-OS 1246173, DE-OS 1247553), which additionally may contain butadien/styrol or butadien/acrylnitrile-copolymer, (U.S. Pat. No. 3,314,425) and such from polyurethane (DE-OS 2103590, GB-PS 1065994, GB-PS 1253845, U.S. Pat. No. 3,157,178, U.S. Pat. No. 3,648,692, U.S. Pat. No. 3,975,567, U.S. Pat. No. 3,978,855). The hydrolyse products of the cross linked vinylacetate/methacrylate-copolymer can absorb, for example, 100 times of its own weight of water or wound exsudate, the cross linked polyacrylamide up to 70 times and the cross linked poly-y-vinylpyrrolidone at least 15 times.

Most of the wound dressings are fabrics or texture materials of fiber-like articles, i.e., they are being used in form of premade flat shaped articles. The covering of the wounds with particulate matter, like powders or the like, is performed comparatively seldom, although they have great advantages over flat shaped wound dressings, in particular with uneven or fissued wounds.

Useable particulate materials for wound coverings are described in DE-OS 2403260, for example. These are micro pearls of cross linked polysaccharide and polysaccharide derivatives, in particular cross linked dextrane which are applied directly on the wound. It is further known, that for the same purpose spherical regenerated cellulose particles can be used. Both materials have a high degree of absorbability for wound secretions and are able to remove bacteria, fungi, toxins, inflammation mediators (prostaglandine) and plasma proteins (fibrinogen-fission products).

Despite of many proven positive advantages, the two particulate materials have still some disadvantages which limit a wide use thereof. The particles which are build up from cross linked dextranes, whose gel matrix has genuine pores, neither in the dry state, nor in the wet state, do swell during contact with water or watery solutions with a strong volume enlargement and result in a gel layer which reduces the gas permeability therein. This disadvantage is overcome with the regenerated cellulose particles which have a macroporous structure and therefore absorb water without swelling, but their porosity causes to absorb non-watery medium, for example, organic solvents, which can have unfavorable effects at different types of applications; their sterilization with γ rays is combined with a yellow to brownish discoloration. The aforementioned particulate materials can be made in accordance with known methods, for example, by acidifying the cellulose particles with emulsified cellulose solvents (SE-PS 382066, U.S. Pat. No. 3,597,350), by instilling viscose solutions in suitable coagulation baths (JP-PS 73.21738, JP-PS 73.4082, JP-PS 73.60753), by a short time heating of particulate cellulose ester, like, for example, cellulose acetate in silicon oil to 290°–300° C. (JP-PS 78.07759, JP-PS 78.86749), or by thermic coagulation of vixcose dispersions (CS-US 172640, DD-PS 118887, DE-OS 2523839, U.S. Pat. No. 4,055,510). However, the cellulose particles which are obtained by this method result in an absorption capable wound dressing of the aforementioned quality if they are so dried that their macroporosity is preserved. In accordance with the present state of the art, this can only be achieved with special drying methods which are expensive and economically unfavorable.

SUMMARY OF THE INVENTION

It is therefore an object of the invention to provide a wound dressing which is atoxic and tissue compatible, which is adjustable to the shape of the wound or the effected skin and tissue parts, also uneven and fissued wounds, which removes the exsudate from strongly wetting wounds in a rapid manner and without trauma to the patient, which in addition to the exsudate also absorbs bacteria, fungi, toxins, proteins and prostaglandine, which is sterilisable and after sterilisable and which promotes the granulation and epithelisation, which also tends only at a low degree to swell, due to its genuine or latent macroporosity, so that the gas permeability of the wound covering layer remains substantially unimpaired and which finally is economically advantageous in view of a favorable raw material basis and a simple manner of making, and can also be used in a wide array of applications.

Taking into consideration the raw material situation and taking into consideration the good experiences made with particulate materials, it is an object of the invention to develop a wound dressing of the aforementioned quality on the basis of cellulose specimen and a method for making that dressing. Surprisingly, it had been shown that dry particulate products from mixtures of regenerated cellulose and a carboxylate groups containing polysaccharide derivate, in the following called polysaccharide derivative, result in an absorbing wound dressing of the desired quality, surprisingly because the added polysaccharide derivatives to the regenerated cellulose act plasma coagulating and therefore hemostatic, which should result in an undesirable scabbing of the wound; however, such a scabbing does not occur; the particulate products which are applied onto the wound, the spherical particles or granulates which may have a diameter of >10 μ, absorb watery wound secretions of a given consistency and simultaneously bacteria, fungi, toxins, proteins, and inflammation mediators rapidly and substantially painless, so that wound infections are reduced or prevented, the wound dries quickly but remains elastic. The granulated structure of the particles which is preserved in the exsudate saturated state also stimulates the granulation and epithelisation and thereby the high form stability which is obtained by the comparable low degree of swelling of the particles and therefore assures a good ventilation.

The polysaccharide derivatives which are admixed with regenerated cellulose and which in their deformed state result in the inventive wound dressing must be soluble in water to about at least 50%; suitable are, for example, sodium carboxymethyl cellulose, sodium carboxymethyl starch and sodium alginate. Their constituent in the polymer mixture is 3 to 30%.

The inventive particulate products made from mixtures of regenerated cellulose and polysaccharide derivatives are characterized with respect to the spherical particles made from pure regenerated cellulose in that the required drying during the manufacturing process can be performed in conventional manner. Thereby, the originally present pore system collapses due to the shrinking of the particle, but when wetted with water during application conditions it is substantially regenerated, so that the particles with their absorption capability do not only compare with the particles made from pure cellulose, but they are supperior thereto. Thereby, the hydrophilic character of the used polysaccharide derivatives and their chromatographic separation capabilities are additionally positively noticeable. While the pure cellulose particles can only absorb germs into the interparticulate capillary spaces, wherein they are retained rather loosely, the particular inner structure of the inventive particles and the ionic character of the polysaccharide derivatives provide a considerably more retentive binding.

A further advantage consists in that the water absorption capability and the kinetic of the water or exsudate absorption can be adjusted in wide limits over the manufacturing process, so that an improved adjustment for different requirements is made possible.

Furthermore, a considerable advantage is that the inventive particulate products retain their positive effect in the presence of glycerol or polyalkylene glycoles, which enable the making of paste-like preparations; moreover, it had been shown that an application of smaller quantities of glycerol or polyethylen glycol preferably 5 to 30%, prevents damages during the ray-chemical sterilisation, which otherwise would occur in that the production parameter would be impaired and a yellow coloration would show.

DETAILED DESCRIPTION OF THE INVENTION

The inventive particulate products are conventionally applied at a layer thickness of up to 5 mm onto the wound and, if need be, secured by a light conventional compression bandage. The replacing of the wound dressing which should be performed after saturation with wound exsudate, but not later than after 14 to 20 hours, is rather simple and effortless, for example, by rinsing off the particle layer with water or physiological sodium chloride solution, so that a fresh application of the particulate material may be performed.

The aforedescribed wound dressing with the desired quality is obtained in accordance with the invention in that one adds to a technical conventional viscose solution a polysaccharide derivative of the aforementioned specification at a constituent of 5 to 50% with respect to the total mass of the polymer mixture in the viscose solution, that this mixture thermically coagulates, that the coagulate is purified, is wetted with 5 to 30% of a polyalkyle glycol and is dried. The particulate structure of the products can be generated before or after the coagulation. In a specific embodiment the particle formation occurs in that the viscose solution which contains the additional polysaccharide derivative is thermically coagulated and regenerated in accordance with known techniques, for example, by dispersing in an organic liquid which is not miscible with water, by instilling it and by heating to temperatures of 50° to 100° within 30 to 90 min.

In a further embodiment of the method, the viscose solution which contains the polysaccharide derivative is treated under comparable condition but without a previous fine dispersion, whereby the coagulate is obtained in form of plates, rods or blocks, which are mechanically crushed in a suitable manner. The obtained fine particle sized crumbled masses result in powdery granulated products, after washing and drying, and which have to be subjected to a dry grinding, if need be, so as to obtain the desired particle spectrum.

The obtained particulate products are subjected to a series of washing operations with low molecular alcohols, preferably methanol or ethaol, or ketons, preferably aceton, with watery solutions of these alcohols and/or ketones and/or with water or watery solutions, like, for example, diluted acids or alkalines for cleaning and simultaneously for controlling the product characteristics, whereby 5 to 50% of the admixed polysaccharide derivative are washed out.

The drying of these products can be performed with known simple methods, for example, on a fluid bed drier, whereby the particles are released from the superflous last washing liquid by means of centrifuging or vacuuming, before subjected to the drying process, whereby the washing liquid advantageously should not be a non-watery or partially non-watery medium which already contains an addition of polyalkyle glycol or glycerol. As added polysaccharide derivatives one considers sodium carboxymethyl cellulose, sodium carboxymethyl starch and sodium alginate.

In a preferred embodiment of the method sodium carboxymethyl cellulose with an average substitution degree (DS) of 0.4 to 1.0 is used as the polysaccharide derivative.

Depending from the type and the quantity of the added sodium carboxymethyl cellulose, as well as of the process execution during the aftertreatment and drying, one obtains more or less shrunk, substantially isometric particles which are able to absorb between 1.5 and 20 ml water per gram dry substance, whereby the particles which were recovered by dispersion are substantially spherical and have a comparatively smooth surface and the particles which are made differently have an irregular shape as well as a rougher surface, however without disadvantageously influencing the essential product characteristic magnitude.

Basically, the inventive particles which consist of the polymer mixtures can be dried protectively in the same manner as the pure regenerated cellulose materials. In this, one obtains products which are less shrunk and which already have a high macroporosity macroporosity in the dry state. If the polysaccharide derivatives are added to the viscous solution in dissolved form and in such a concentration that a reduction of the total polymer concentration of the solution results, or if larger quantities of the polysaccharide derivatives are removed from the wet particles in the subsequent treatment steps, one obtains materials which have a strongly increased space volume with respect to the pure regenerated cellulose products, after a protective drying.

The following examples describe the application of the inventive suggested wound dressing, as well as its making.

EXAMPLE 1

The strongly secreting wound of a patient with an Ulcus cruris was covered with a 3 mm thick layer of the inventive wound dressing. The wound dressing consisted of dry spherical regenerated cellulose particles which were sterilised with $\gamma$ rays and which contained 10% sodium carboxymethyl cellulose, had a median particle size of 0.2 mm and a water absorption of 3.2 ml/g. The water absorption was defined in accordance with the centrifuging method (Cell. Chem. Technol. 21, (1978) 419–428) and states the retained water quantity in the pore system of the cellulose particle (water retention capability). The wound dressing was changed daily in that the absorbed material was rinsed off with physiological sodium chloride and a fresh 3 mm thick wound dressing was applied. The wound was clearly cleansed and was almost dry, after 5 days, and after 9 days, one could apply a conventional dressing.

EXAMPLE 2

A patient suffered from an infected superficial wound after a post traumatic ostitis. The open wound was covered with a 3 mm thick layer of a wound dressing which consisted of granular-like regenerated cellulose particles which were sterilised with $\gamma$ rays and which contained 20% sodium carboxymethyl cellulose and 5% glycerol and had a particle size of 0.1 to 0.5 mm and a water absorption of 4.6 ml/g.

The wound dressing was changed daily, whereby the removal of the wound dressing was performed by means of a spatula. A clear reduction of the inflammation was clearly shown after 5 days, as well as an obvious cleansing and healthy granulation of the wound. A conventional wound dressing could be applied after 8 days.

EXAMPLE 3

The infected strongly wetted wound of a patient with large area burns was covered with a 3 mm thick layer of a wound dressing which consisted of dry spherical regeneration cellulose particles, which were sterilised with $\gamma$ rays, which contained 10% of sodium carboxymethyl cellulose and 20% polyethyl glycol (relative molecular mass 600) and had a particle size of 0.2 to 0.3 mm and a water absorption of 2.5 ml/g.

The wound dressing was changed daily, whereby the removal of the fully absorbed material was performed without any injury to the base of the wound. The wound was clean and dry after 7 days and at the edge thereof an apithelisation of the defect started. The wound was ripe for transplantation after 12 days.

EXAMPLE 4

For making the inventive wound dressing, a mixture of 50 g viscose (8% cellulose, 6% sodium hydroxide, xanthogenation with 35% carbon disulfide, with respect to cellulose) and 50 g watery 4% solution of a sodium carboxymethyl cellulose (CMC) with an average substitution degree (DS) of 0.3 in 150 ml chlorbenzene which contained 0.05 oil acid as an emulsifier was dispersed by means of a stirrer. The obtained droplets were coagulated at a temperature of 90° C. under further stirring for about 30 minutes. The generated product from high swelled spherical particles was separated from the chlorbenzene and water by means of a vacuum. For preparations, portions of 20 g of the recovered wet crude product was used with a polymer content of about 1.3 g, as in some of the following examples. Purification was performed with different modifications as follows:

(a) The particles were washed 4 times with 100 ml watery methanol (80 Vol.-%) alkaline and salt free, finally treated with 70 ml ethanol for 10 minutes.

(b) The particles were purified in accordance with the following method steps:
  100 ml water, 10 minutes, 90° C.
  100 ml water, 10 minutes, 90° C.
  100 ml water, 10 minutes, room temperature
  70 ml ethanol, 10 minutes, room temperature (c) The particles were purified in accordance with modification (b), however with the difference that a washing out was performed for three times with water at a temperature of 90° C.

(d) The particles were purified in accordance with the following method steps:
  100 ml watery methanol, 80 Vol.-%, 10 minutes, room temperature
  100 ml watery methanol, 80 Vol.-, 10 minutes, room temperature
  100 ml water, 10 minutes, 90° C.
  100 ml water, 10 minutes, room temperature
  70 ml ethanol, 10 minutes, room temperature The purified particles were suctioned off, dried at 105° C. and showed the analytical data in the following table:

|     | CMC-content | Water absorption | Solubles |
| --- | --- | --- | --- |
| (a) | 33,3% | 5,9 ml/g | 7,4% |
| (b) | 26,4% | 6,2 ml/g | 3,2% |
| (c) | 15,9% | 7,3 ml/g | 1,5% |
| (d) | 28,1% | 7/5 ml/g | 1,0% |

EXAMPLE 5

For making the inventive wound dressing, spherical particles analog to example 4 were used, however by using a CMC with a DS of 0.5 as a mixing component and were produced in different charges. The spherical particles of these charges were purified in accordance with modification (b) in example 4 and after drying at a residue solubility of 2 to 4% the following, within the error limits, correlative values for the water absorption:

|   | Water absorption |   | Water absorption |
| --- | --- | --- | --- |
| Charge 1 | 6,1 ml/g | Charge 5 | 6,9 ml/g |
| Charge 2 | 6,1 ml/g | Charge 6 | 6,6 ml/g |
| Charge 3 | 5,9 ml/g | Charge 7 | 6,3 ml/g |
| Charge 4 | 6,5 ml/g |   |   |

EXAMPLE 6

For making the inventive wound dressing, spherical particles analog to example 4 were used, however by using a CMC with a DS of 0.7 as a mixing component and was aftertreated and purified in accordance with different modifications:

(a) The particles were purified in accordance with the following method steps:
  100 ml methanol, 10 minutes room temperature
  100 ml methanol, 10 minutes room temperature
  100 ml water, 10 minutes 90° C.
  100 ml water, 10 minutes room temperature
  70 ml ethanol, 10 minutes room temperature (b) The particles were purified in accordance with the following method steps:
  100 water, 10 minutes, 90° C.
  100 ml water, 10 minutes, 90° C.
  70 ml ethanol, 10 minutes, room temperature The purified and aftertreated particles were separated from the liquid phase, dried at 105° C. dried and showed the following values:

|     | Water absorption | Soluble |
| --- | --- | --- |
| (a) | 9,6 ml/g | 3,4% |
| (b) | 5,2 ml/g | 2,0% |

EXAMPLE 7

For making the inventive wound dressing, 25 g of a mixture of 12.5 g vixcose and 12.5 g watery 4% CMC (DS 0.5) were decanted into a cylindrical vessel of about 10 mm diameter and was coagulated thermically at 90° C. for about 90 minutes. The material was crushed to a fine particle granulate of about 1 mm and less particle size and was purified in accordance with modification (a) in example 6. The powdery granulate product which was obtained after drying at 105° C. had a water absorption of 7.6 ml/g.

EXAMPLE 8

For making the inventive wound dressing, spherical particles analog to example 4 were used, however by using a CMC (DS 0.7) partially cross linked with epichlorhydrin, with a solubility in water of still about 50%. The mixing component was admixed to the vixcose substantially dissolved in normal sodium wash. The obtained particles were purified in accordance with modification (d) in example 4 and showed a water absorption of 14.0 ml/g at a residue solubility of 0.6%, after drying at a temperature of 105° C.

EXAMPLE 9

In accordance with the embodiment in example 4, spherical particles were made by adding sodium carbomethyl starch and sodium alginate, purified in accordance with modification (d) in example 4 and dried at 105° C. The products showed the following values for the water absorption:
  with sodium carboxymethyl starch: 5.7 ml/g; soluble: 4.2%
  with sodium alginate: 3.1 ml/g; soluble: 1.5%

We claim:

1. Absorbing wound dressing of a granulate particulate cellulose material, comprised of spherical particles consisting of a mixture of regenerated cellulose with 3 to 30 weight % of carboxylate groups containing polysaccharide derivative selected from the group consisting of sodium carboxymethyl cellulose, sodium carboxymethyl starch and sodium alginate, the mixture being wetted with watery liquids and after the wetting forming a non-gel air-permeable wound dressing having a macroporous structure and a low degree of swelling so that the absorbing property of the dressing is such that it can absorb wound secretions in a quantity of 1.5 to 20 ml/g of dry substance, including bacteria, toxins, proteins and wound inflammation metiators, whereby the dressing is able to remove ex udate from strongly wetting wounds in a rapid manner.

2. Absorbing wound dressing in accordance with claim 1, further containing 5 to 90 weight % of glycol or polyalkyl glycol.

3. Absorbing wound dressing in accordance with claim 1, wherein the diameter of said spherical particles is >10 μ.

4. Absorbing wound dressing of a granulate particulate cellulose material, comprised of spherical particles consisting of a mixture of regenerated cellulose with 3 to 30 weight % of carboxylate groups containing sodium carboxymethyl cellulose, the mixture being wetted with watery liquids and after the wetting forming a non-gel air-permeable wound dressing having a macroporous structure and a low degree of swelling so that the absorbing property of the dressing is such that it can absorb wound secretions in a quantity of 1.5 to 20 ml/g of dry substance, including bacteria, toxins, proteins and wound inflammation mediators, whereby the dressing is able to remove excudate from strongly wetting wounds in a rapid manner.

5. Absorbing wound dressing of a granulate particulate cellulose material, comprised of spherical particles consisting of a mixture of regenerated cellulose with 3 to 30 weight % of carboxylate groups containing sodium carboxymethyl cellulose, the mixture being wetted with polyalkyl glycol and after the wetting forming a non-gel air-permeable wound dressing having a macroporous structure and a low degree of swelling so that the absorbing property of the dressing is such that it can absorb wound secretions in a quantity of 1.5 to 20 ml/g of dry substance, including bacteria, toxins, proteins and wound inflammation mediators, whereby the dressing is able to remove excudate from strongly wetting wounds in a rapid manner.

* * * * *